United States Patent
Cheng

(10) Patent No.: US 9,486,330 B2
(45) Date of Patent: Nov. 8, 2016

(54) MINIMALLY INVASIVE METHOD AND SURGICAL TOOLS FOR TRANS-PSOAS APPROACH

(71) Applicant: Bones and Spine Surgery Inc., Redlands, CA (US)

(72) Inventor: Wayne K. Cheng, Redlands, CA (US)

(73) Assignee: Bones and Spine Surgery Inc., Redlands, CA (US)

(*) Notice: Subject to any disclaimer, the term of this patent is extended or adjusted under 35 U.S.C. 154(b) by 44 days.

(21) Appl. No.: 14/195,671

(22) Filed: Mar. 3, 2014

(65) Prior Publication Data
US 2014/0296982 A1    Oct. 2, 2014

Related U.S. Application Data

(60) Provisional application No. 61/771,710, filed on Mar. 1, 2013, provisional application No. 61/833,768, filed on Jun. 11, 2013.

(51) Int. Cl.
*A61F 2/44* (2006.01)
*A61B 17/88* (2006.01)
(Continued)

(52) U.S. Cl.
CPC .............. *A61F 2/4611* (2013.01); *A61B 17/02* (2013.01); *A61B 17/7055* (2013.01);
(Continued)

(58) Field of Classification Search
CPC ...... A61F 2/4611; A61F 2/4455; A61F 2/44; A61F 2/4405; A61F 2/4465; A61F 2/46; A61F 2002/4475; A61F 2/442–2/447; A61B 17/02; A61B 17/7055; A61B 17/88; A61B 17/2017; A61B 17/0256; A61B 17/0262; A61B 17/8872; A61B 17/70; A61B 17/7062; A61B 17/885–17/8858
USPC ................................ 623/17.11, 17.15, 17.16
See application file for complete search history.

(56) References Cited

U.S. PATENT DOCUMENTS 5,167,223 A   12/1992   Koros et al.
5,171,278 A   12/1992   Pisharodi
(Continued)

FOREIGN PATENT DOCUMENTS

WO   2007022194 A2   2/2007
WO   2011041038 A3   5/2011
(Continued)

OTHER PUBLICATIONS

International Preliminary Report on Patentability for International Application PCT/US2014/019993, Completed Feb. 24, 2015, Mailed Mar. 2, 2015, 3 Pgs.
(Continued)

*Primary Examiner* — Jacqueline Johanas
*Assistant Examiner* — Tessa Matthews
(74) *Attorney, Agent, or Firm* — KPPB LLP

(57) ABSTRACT

Methods, surgical tools and a surgical system for performing spinal fixation using a lateral trans-psoas approach through a vertebral body into the disc space between that vertebral body and an adjacent vertebral body are provided. The approach, tools and system are adapted for use in fixing the L-5 and S-1 vertebral bodies. It should be understood that the methods and tools described can also be used for disc fusion where insertion proceeds from an inferior vertebral body to a superior vertebral body, and also cases where the fusion occurs across multiple disc spaces fusing more than two vertebrae.

14 Claims, 18 Drawing Sheets

(51) Int. Cl.
*A61F 2/46* (2006.01)
*A61B 17/02* (2006.01)
*A61B 17/70* (2006.01)
*A61F 2/30* (2006.01)
*A61B 5/0492* (2006.01)
*A61B 5/00* (2006.01)
*A61B 17/00* (2006.01)
*A61B 17/22* (2006.01)
*A61B 17/32* (2006.01)

(52) U.S. Cl.
CPC .......... *A61F 2/4455* (2013.01); *A61B 5/0492* (2013.01); *A61B 5/4566* (2013.01); *A61B 17/025* (2013.01); *A61B 2017/00309* (2013.01); *A61B 2017/00946* (2013.01); *A61B 2017/0256* (2013.01); *A61B 2017/22061* (2013.01); *A61B 2017/320048* (2013.01); *A61F 2002/30912* (2013.01); *A61F 2002/4495* (2013.01); *A61F 2002/469* (2013.01); *A61F 2002/4692* (2013.01)

(56) References Cited

U.S. PATENT DOCUMENTS

| | | | |
|---|---|---|---|
| 5,180,381 | A | 1/1993 | Aust et al. |
| 6,436,140 | B1 | 8/2002 | Liu et al. |
| 6,582,467 | B1 | 6/2003 | Teitelbaum et al. |
| 7,758,644 | B2 | 7/2010 | Trieu et al. |
| 7,909,871 | B2 | 3/2011 | Abdou et al. |
| 7,951,199 | B2 | 5/2011 | Miller et al. |
| 8,137,284 | B2 | 3/2012 | Miles et al. |
| 8,187,327 | B2 | 5/2012 | Edidin et al. |
| 8,287,597 | B1* | 10/2012 | Pimenta et al. ............ 623/17.16 |
| 8,303,515 | B2 | 11/2012 | Miles et al. |
| 8,328,852 | B2 | 12/2012 | Zehavi et al. |
| 8,470,004 | B2 | 6/2013 | Reiley et al. |
| 8,696,559 | B2 | 4/2014 | Miles et al. |
| 8,747,307 | B2 | 6/2014 | Miles et al. |
| 8,790,406 | B1 | 7/2014 | Smith et al. |
| 2002/0016583 | A1* | 2/2002 | Cragg ........................ 604/500 |
| 2003/0216771 | A1 | 11/2003 | Osypka et al. |
| 2004/0034430 | A1 | 2/2004 | Falahee et al. |
| 2005/0256575 | A1 | 11/2005 | Pavlov et al. |
| 2007/0083086 | A1* | 4/2007 | LeVahn et al. ............... 600/210 |
| 2007/0276494 | A1 | 11/2007 | Ferree |
| 2009/0012527 | A1 | 1/2009 | Mignucci et al. |
| 2009/0099610 | A1 | 4/2009 | Johnson et al. |
| 2009/0112261 | A1* | 4/2009 | Barry ........................ 606/246 |
| 2009/0216234 | A1 | 8/2009 | Farr et al. |
| 2010/0286784 | A1* | 11/2010 | Curran et al. ............. 623/17.16 |
| 2011/0029083 | A1 | 2/2011 | Hynes et al. |
| 2011/0065999 | A1 | 3/2011 | Manzanares et al. |
| 2011/0125266 | A1 | 5/2011 | Rodgers et al. |
| 2011/0257684 | A1 | 10/2011 | Sankaran et al. |
| 2011/0319995 | A1 | 12/2011 | Voellmicke et al. |
| 2012/0029518 | A1* | 2/2012 | Blackwell et al. ............. 606/79 |
| 2012/0035730 | A1 | 2/2012 | Spann et al. |
| 2012/0172797 | A1 | 7/2012 | Adams et al. |
| 2012/0226320 | A1 | 9/2012 | Kang et al. |
| 2012/0316652 | A1 | 12/2012 | Renganath et al. |
| 2013/0053780 | A1 | 2/2013 | Goode et al. |
| 2013/0085535 | A1* | 4/2013 | Greenhalgh et al. ......... 606/279 |
| 2013/0138214 | A1 | 5/2013 | Greenhalgh et al. |
| 2014/0100580 | A1 | 4/2014 | Yu et al. |

FOREIGN PATENT DOCUMENTS

| | | |
|---|---|---|
| WO | 2014134614 A1 | 9/2014 |
| WO | 2014134614 A9 | 12/2014 |

OTHER PUBLICATIONS

International Search Report and Written Opinion for International Application PCT/US14/19993, completed Apr. 30, 2014, Mailed Jun. 2, 2014, 10 Pgs.

Aghayev et al., "Mini-open lateral retroperitoneal lumbar spine approach using psoas muscle retraction technique. Technical Report and initial results on six patients", Eur. Spine J., 2013, vol. 22, pp. 2113-2119.

Anand et al., "Minimally Invasive Multilevel Percutaneous Correction and Fusion for Adult Lumbar Degenerative Scoliosis: A Technique and Feasibility Study", Journal of Spinal Disorders & Techniques, Oct. 2008, vol. 21, Issue 7, pp. 459-467.

Atalay et al., "Vertebral reconstruction using the telescopic plate spacerthoracoumbar (TPS-TL) device", J. Spinal Disord Tech., Jul. 2010, 23(5), pp. 338-346 (abstract 1 pg).

Bergey et al., "Endoscopic Lateral Transpsoas Approach to the Lumbar Spine", Spine, Aug. 2004, vol. 29, Issued 15, 1 pg. (abstract).

Blecher, "Implanting Expanding Cages to Reconstruct the Spine: Patient Cases", printed Nov. 6, 2015 from http://www.spineuniverse.com/print/exams-tests/devices/impnating-expanding-cages-reco . . . , 4 pgs.

Blecher, "Vertebral Body Reconstruction Using Expandable Cages", Printed Nov. 6, 2015 from http://www.spineuniverse.com/print/exams-tests/devices/vertebral-boyd-reconstruction-usi . . . , 3 pgs.

Blecher, "Vertebral Body Reconstruction Using Expandable Cages", spineuniverse; Sep. 7, 2012, printed from http://www.spineuniverse.com/exams-tests/devices/vertebral-body-reconstruction-using . . . , 2 pgs.

Bluecross Blueshield, "Minimally Invasive Lumbar Interbody Fusion", Mar. 2012, printed from https://www.bcbsal.org/providers/policies/final/182.pdf, 22 pgs.

Bozkus et al., "Transvertebral interbody cage and pedicle screw fixation for high-grade spondylolisthesis", J. Neurosurg, Jan. 2004, 100(1 Suppl Spine) pp. 62-65 (abstract 2 pgs).

Chou et al., "Adjacent-level bertebral body fractures after expandable cage reconstruction", J. Neurosurg.Spine, Jun. 2008, 8(6), 584-588 (abstract 2 pgs).

De Maat et al., "Removal of the Charite Lumbar Artificial Disc Prosthesis: Surgical Technique", Journal of Spinal Disorders & Techniques, Jul. 2009, vol. 22, Issue 5, Abstract, 1 pg.

Frantzides et al., "L5-S1 Laparoscopic Anterior Interbody Fusion", JSLS, 2006, vol. 10, pp. 488-492.

Health Net, "Axial Lumbar Interbody Fusion (AxiaLIF) and Lateral Lumbar Interbody Fusion (XLIF)", National Medical Policy, Mar. 2008, 18 pgs.

Hood et al., "Minimally Invasive Extreme Lateral Trans-Psoas Approach to The Lumbar Spine: Applications and Techniques", Spine Surgery, Mar. 28, 2012, printed from http://cdn.intechopen.com/pdfs/34184/InTech-Minimally_invasive_extreme_lateral_trans_psoas_approach_to_the_lumbar_spine_applications_and_techniques.pdf, 37 pgs.

Kepler et al., "Anatomy of the psoas muscle and lumbar plexus with respect to the surgical approach for lateral transpsoas interbody fusion", Eur. Spine J. 2001, vol. 20, pp. 550-556.

Manwaring et al., "Management of sagittal balance in adult spinal deformity with minimally invasive anterolateral lumbar interbody fusion: a preliminary radiographic study", J. Neurosurg. Spine, 2014, vol. 20, pp. 515-522.

Obenchain, "Laparoscopic Lumbar Discectomy: Case Report", Journal of Laparoendoscopic Surgery, 1991, vol. 1, No. 3, pp. 145-152.

Oppenheimer et al., "Minimally invasive spine technology and minimally invasive spine surgery: a historical review", Neurosurg. Focus, 2009, vol. 27, No. 3, 15 pgs.

* cited by examiner

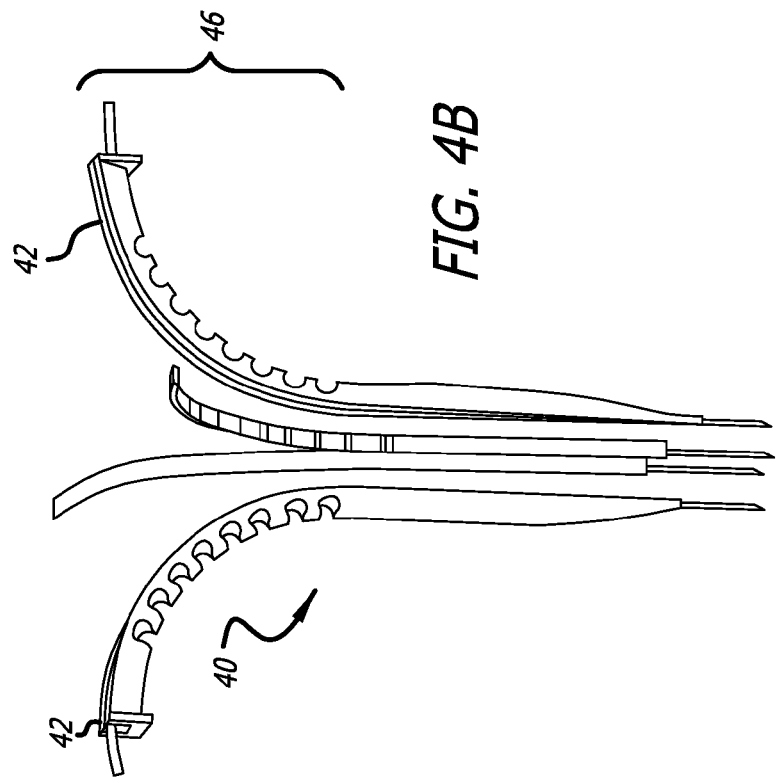
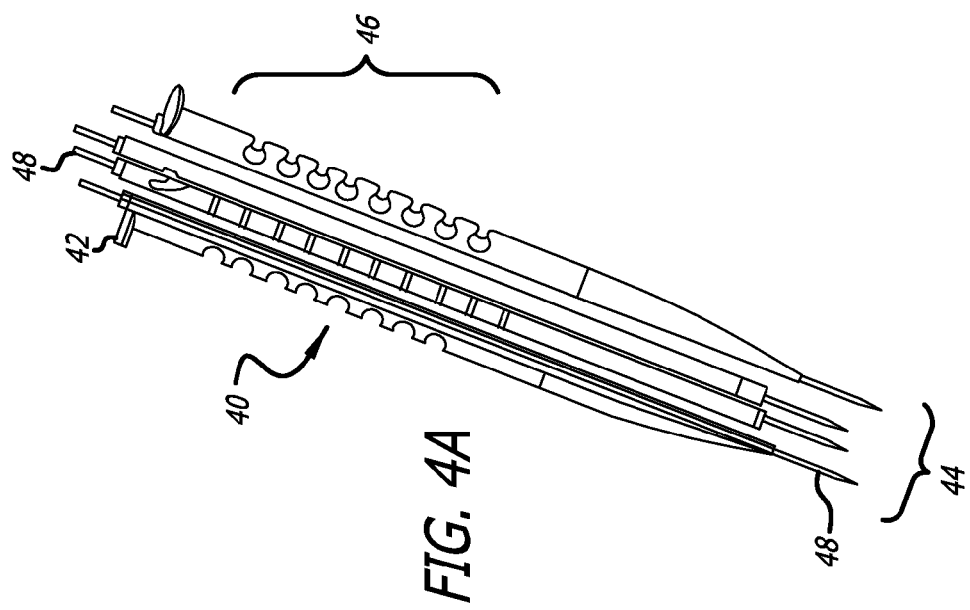

MINIMALLY INVASIVE METHOD AND SURGICAL TOOLS FOR TRANS-PSOAS APPROACH

FIELD OF INVENTION

Surgical tools for a minimally invasive trans-psoas approach; and more particularly to a trans-psoas approach for the insertion of a trans-vertebral body cage are provided.

BACKGROUND

Patients that experience chronic discomfort in their backs often require remedial surgery in order to correct structural problems such as disc degeneration. This degeneration may come in many forms, but invariably results in an unacceptable variance in the alignment and/or spacing of one or more portions of the spine. It is acknowledged that maintenance of the normal curvature of the lumbar spine is preferable, and so when corrective surgery is required, it is important to re-establish the normal biomechanical arrangement, and to restore the profile of the spine.

A wide variety of prior art techniques have been used to correct spinal posture and the placement and spacing of the individual vertebrae. One common technique where disc degeneration has occurred is to remove the degenerated disc, distract the disc space, and fuse the adjacent vertebrae together. These interbody fusions attempt to address the instability caused by degenerative discs and facet joints by using implants to restore the natural arrangement of the spine and stabilizing screws, and rods to anchor the spine in place while the fusion of bones is accomplished. In particular, most of these methods require the insertion of metal cages packed with bone or ortho-biological compounds (osteoinductive/osteoconductive) within the disc space that serve to fuse the adjacent vertebrae.

Again, there are innumerable techniques and surgical approaches to accomplish this interbody fusion. Traditional techniques use either a posterior or anterior approach (see, FIGS. 1a & 1b). In a posterior technique, such as Posterior Lumber Interbody Fusion (PLIF), it is necessary to dissect and retract the back muscles, bones, vessels, ligaments and nerves, which causes a great deal of trauma to the supporting muscles and ligaments of the back. Meanwhile, in an anterior approach, such as Anterior Lumber Interbody Fusion (ALIF), it is necessary to proceed through the abdominal musculature and cavity. This creates the risk of major injury associated with trauma to important vascular structures and/or the genitourinary structures. More recently minimally invasive techniques have been proposed that use a trans-lateral approach, such as Transforaminal Lumber Interbody Fusion, or a trans-sacral approach, such as Axial Lumbar Interbody Fusion (AxiaLIF®). (See, e.g., U.S. Pat. No. 6,899,716 and U.S. Pat. Pub. No 2011/0112373, the disclosures of which are incorporated herein by reference.).

All of these methods have drawbacks, either with regard to the invasiveness of the technique, or, in the case of the trans-sacral approach, the limited area of the spine on which they can be implemented. Now a trans-psoas approach has been proposed that gives access to the disc space from L-1 to L-5. This approach is being increasingly employed to treat common spinal disorders including disc degeneration, spinal deformity and trauma. However, the technique has not been extended to the L-5/S-1 disc space because the anatomy of the pelvis, the lumbarsacral plexus and the iliac vessels make the standard trans-psoas approach extremely dangerous. In addition, the tools to work with this approach are still quite limited and, primarily being borrowed from more traditional techniques, are not well-suited to exploit the minimally invasive nature of the trans-psoas approach. Therefore, a need exists to provide surgical tools and methods adapted for use in a trans-psoas approach to spinal fusion.

SUMMARY OF THE INVENTION

The current invention is directed to a system and method for fusing adjacent vertebrae. More particularly, embodiments of methods, surgical tools, and a surgical system for performing spinal fixation using a lateral trans-psoas approach through a superior vertebral body into the disc space between that superior vertebral body and the disc space between the adjacent inferior vertebral body are described. Additionally, methods of reversing the fusion from an inferior to superior vertebral bodies, and in extending the fusion across multiple vertebrae are described.

In some embodiments the invention is directed to a method for performing a lateral trans-psoas spinal fusion procedure including:
  forming a surgical opening and passageway through the lumbar plexus at the fusion site;
  forming an opening in the lateral edge of a primary vertebral body to allow access to the disc space between the primary vertebral body and an adjacent vertebral body;
  exposing the bony endplate of the adjacent vertebral body;
  preparing and distracting the disc space between the primary and adjacent vertebral bodies;
  inserting an interbody cage through the primary vertebral body and the disc space, and anchoring the cage in at least the primary and adjacent vertebral bodies;
  expanding the interbody cage into the disc space; and
  inserting a cage screw to stabilize the primary vertebral body and an adjacent vertebral body.

In embodiments, the primary vertebral body is superior to the adjacent vertebral body, and wherein the opening is formed in the superior lateral edge of the superior vertebral body and the cage anchored in at least the superior bony endplate of the inferior vertebral body.

In other embodiments the cage incorporates bone or ortho-biological compounds.

In still other embodiments the superior vertebral body is L-5 and the inferior vertebral body is S-1, and wherein the surgical and opening and passageway proceeds through the lumbar plexus.

In yet other embodiments, the method further includes dilating and retracting tissue disposed between the surgical opening and the insertion point of the cage at the primary vertebral body. In some such embodiments, the step of dilating and retracting tissue includes the use of a retractor having a plurality of separable retractor blades. In other such embodiments, the step of dilating and retracting tissue includes the use of nerve monitoring. In still other such embodiments, the step of dilating and retracting tissue includes the use of fluoroscopic retractor blades.

In still yet other embodiments, the method further includes inserting a guidance wire through the primary vertebral body and the adjacent disc space and into the adjacent vertebral body.

In still yet other embodiments, the step of forming an opening in the lateral edge of the primary vertebral body comprises drilling and reaming. In some such embodiments, the drilling and reaming occurs along a guidance wire. In other such embodiments, the drilling and reaming further comprises harvesting blood and marrow via suction.

In still yet other embodiments, the primary vertebral body is inferior to the adjacent vertebral body, and wherein the opening is formed in the inferior lateral edge of the inferior vertebral body and the cage anchored in at least the inferior bony endplate of the superior vertebral body.

In still yet other embodiments, the fusion occurs across multiple vertebral bodies.

In some embodiments, the dilator/retractor for use in association with a trans-psoas spinal fusion procedure includes an elongated body formed of a plurality of detachably interconnected blades, wherein the blades when detached are movable radially outward relative to each other.

In other embodiments, the blades are formed of a fluoroscopic material.

In still other embodiments, the assembled blades form a conical elongated body.

In yet other embodiments, the conical body includes a passageway through which a guidance wire may be passed.

In still yet other embodiments, the retractor blades are radially deformable at, at least one end thereof. In some such embodiments, the blade include a wire pin for securing the retractor blade in position.

In some embodiments the invention is directed to a stabilizing cage screw for use in association with a trans-psoas spinal fusion procedure including:
  an elongated cylindrically tapered body having proximal and distal ends;
  wherein the proximal end has disposed therein a portion for mating with a suitable drive mechanism; and
  wherein the outer surface of the interbody cage incorporates threading.

In other embodiments, the cage screw further includes a plurality of cutting elements disposed along the outer surface of the cage.

In still other embodiments, the cage screw further includes at least one fenestration in the outer wall thereof, the at least one fenestration.

In yet other embodiments, the cage screw further includes an anchoring screw interconnected with the proximal end of the interbody cage, the anchoring screw being configured to engage a primary vertebral body in a trans-psoas spinal fixation procedure.

In some embodiments the invention is directed to an expandable interbody cage for use in association with a trans-psoas spinal fusion procedure including:
  a cage body formed of a deformable wire mesh;
  an expandable body capable of expanding radially outward disposed within the body of the cage, such that the cage expands from a compressed state to an expanded state under the influence of the expandable body; and
  wherein the expandable body is a balloon having a lumen through which a pressurizing fluid may be fed to affect expansion of said expandable body.

BRIEF DESCRIPTION OF THE DRAWINGS

These and other features and advantages of the present invention will be better understood by reference to the following detailed description when considered in conjunction with the accompanying drawings where.

FIG. 4a provides a side view of a dilator tool in accordance with embodiments of the invention;
FIG. 4b provides a side view of a dilator tool in a retracted position in accordance with embodiments of the invention;
FIG. 4e' provides a detailed schematic view of the retractor tool shown in FIG. 4e;
FIG. 4f' provides a detailed schematic view of the secondary retractor tool shown in FIG. 4f;
FIG. 4g' provides a detailed schematic view of the retractor tools shown in FIG. 4g.

DETAILED DESCRIPTION OF THE EXEMPLARY EMBODIMENTS

In accordance with the figures and description, methods, surgical tools and a surgical system for performing spinal fixation using a lateral trans-psoas approach through a vertebral body into the disc space between that vertebral body and the disc space between the adjacent vertebral body are provided. In particular embodiments, the approach, tools and system are adapted for use in fixing the L-5 and S-1 vertebral bodies. Although some embodiments focus on a superior to inferior fusion across a single disc space, it should be understood that in other embodiments the methods and tools described can also be used for disc fusion where insertion proceeds from an inferior vertebral body to a superior vertebral body, and also cases where the fusion occurs across multiple disc spaces fusing more than two vertebrae.

As discussed, current methods of performing interbody fusions have drawbacks ranging from the invasiveness of the techniques to the limited areas of the spine on which they can be implemented. This disclosure proposes a trans-psoas approach that gives access to the disc space from L-1 to L-5.

However, despite the advantages offered by a trans-psoas approach, they also create technical challenges, including substantial soft tissue interposed between the entry point to the surgery and the interbody space, difficult visualization of the fusion space, and a disc distraction space that has uniquely challenging access.

Figure 1A:
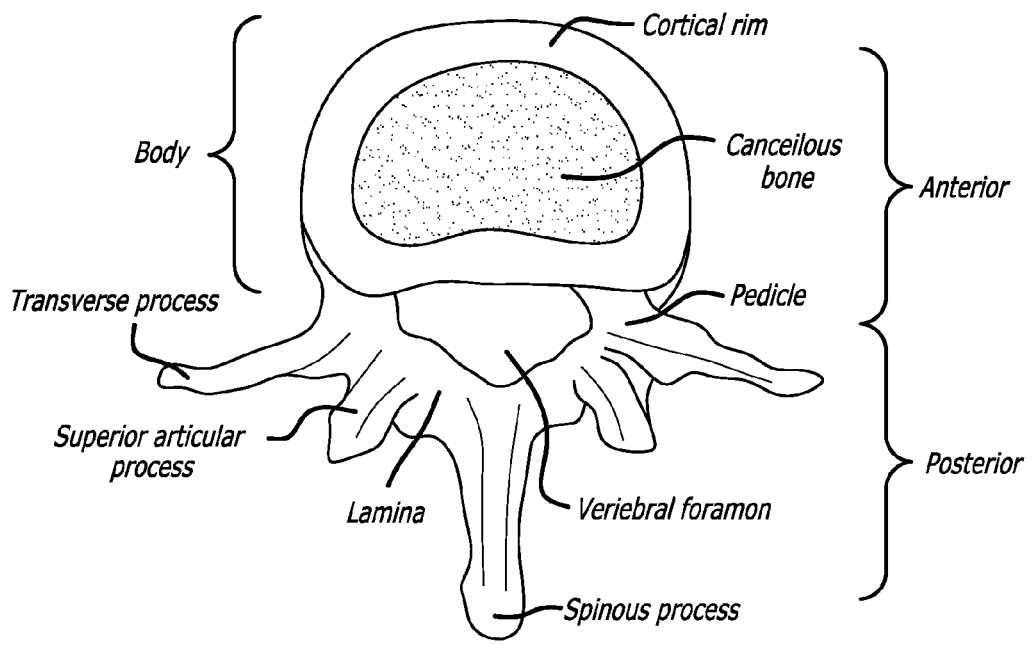
FIG. 1a is a top view of a lumbar body.
Figure 1B:
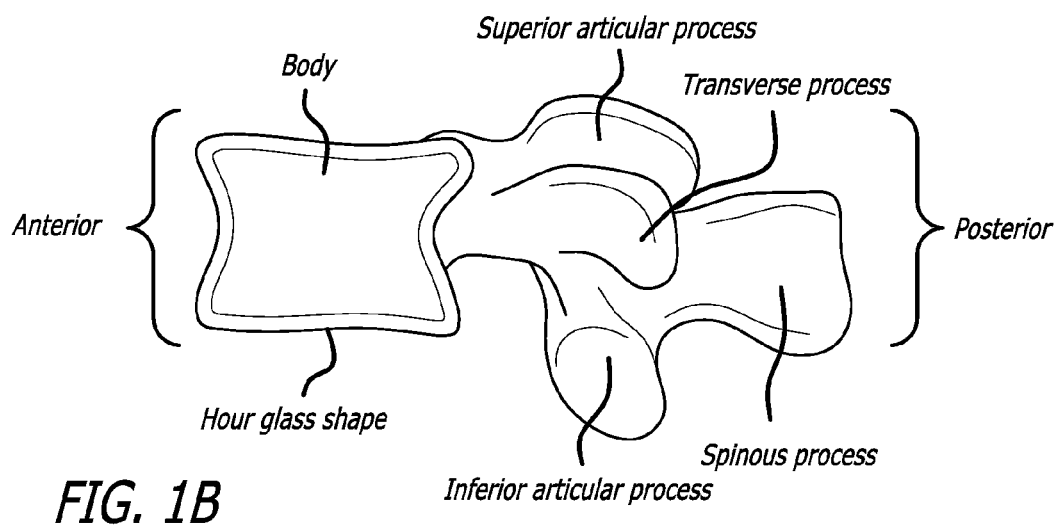
FIG. 1b is a side view of a lumbar body.
Figure 2:
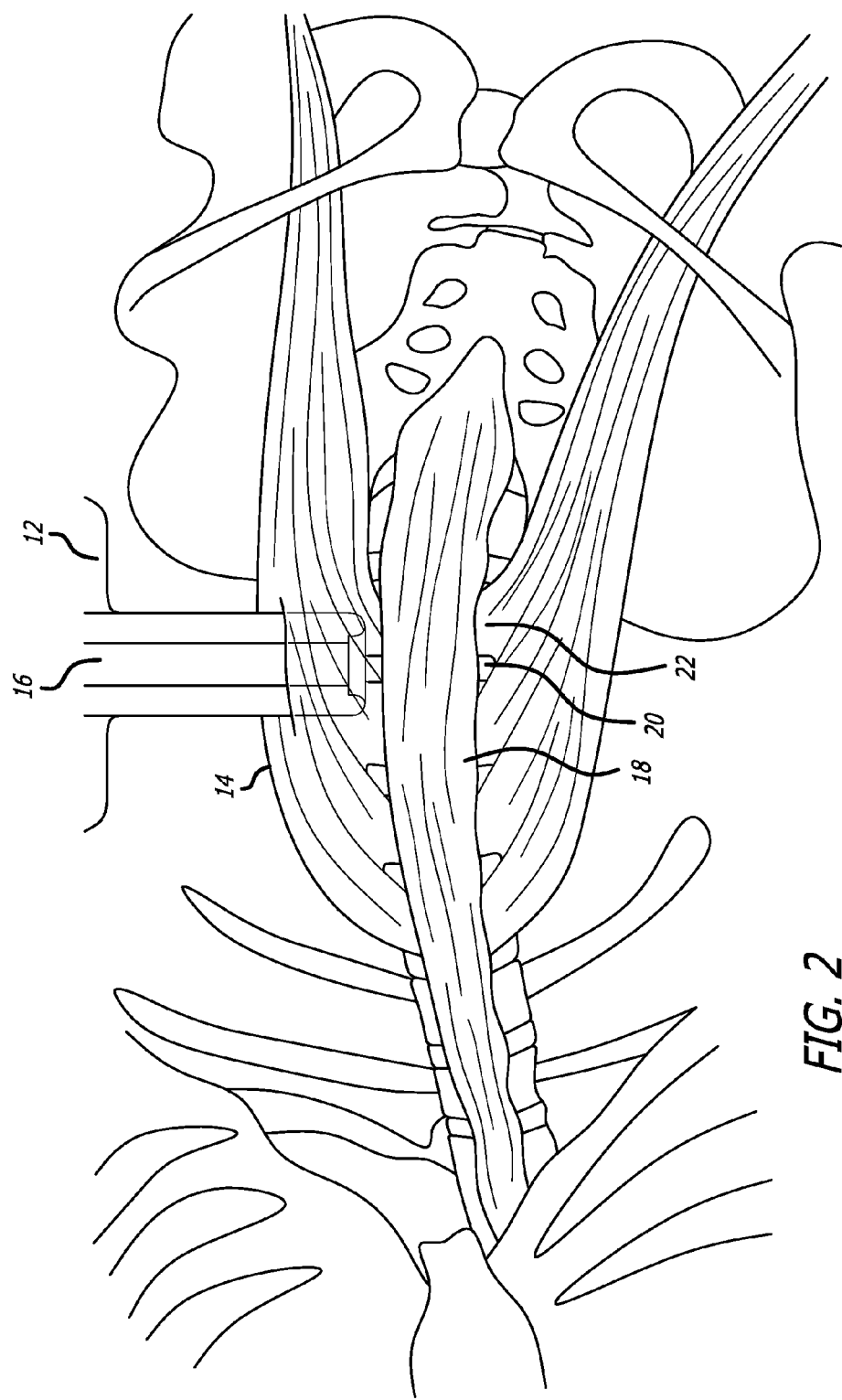
FIG. 2 is an anterior view of the lumbar and sacral regions of the spine where the dilator is positioned in accordance with embodiments of the invention.

As shown in FIG. 2, embodiments of the lateral trans-psoas spinal fusion use an approach that includes a surgical opening (12) and passageway at the fusion site that proceed through the lumbosacral plexus (14). As shown, by deploying retractors (16) it is possible to navigate the lumbosacral plexus and form an opening in the lateral edge of a primary (18) vertebral body to allow access to the disc space (20) between the primary vertebral body and an (22) adjacent vertebral body. As will be discussed in greater detail below, once the bony endplate of the adjacent vertebral body has been exposed, it is then possible to prepare the disc space, for example by distraction, and to insert the necessary interbody and stabilizing cages. Within these cages may be incorporated bone or ortho-biological compounds such that bridging bone may grow within the cage to achieve arthrodesis between the adjacent vertebrae.

In some particular embodiments, the lateral trans-psoas surgical fusion method may be used to fuse the space between any one of the L-5 and S-1 vertebral bodies. In such embodiments, the cage is navigated through the lumbar plexus and thereafter through the body of L-5 from the superior lateral edge of L-5 and therethrough into the disc space between one of L-1 to L-5 and S-1.

Figure 3A:
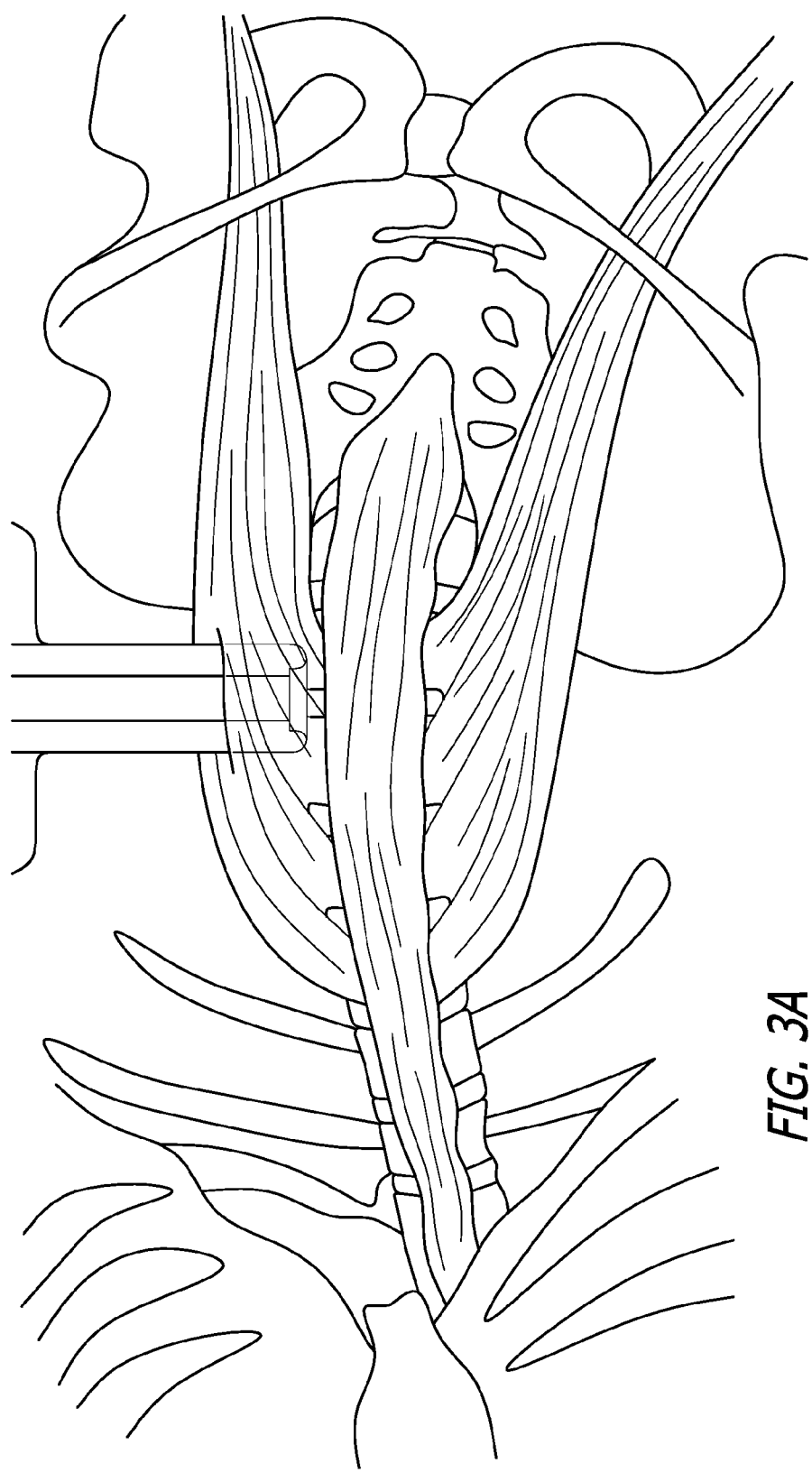
FIGS. 3a to 3e provide schematic views of the procedural steps involved in performing a lateral trans-psoas spinal fusion in accordance with embodiments of the invention.
Figure 3B:
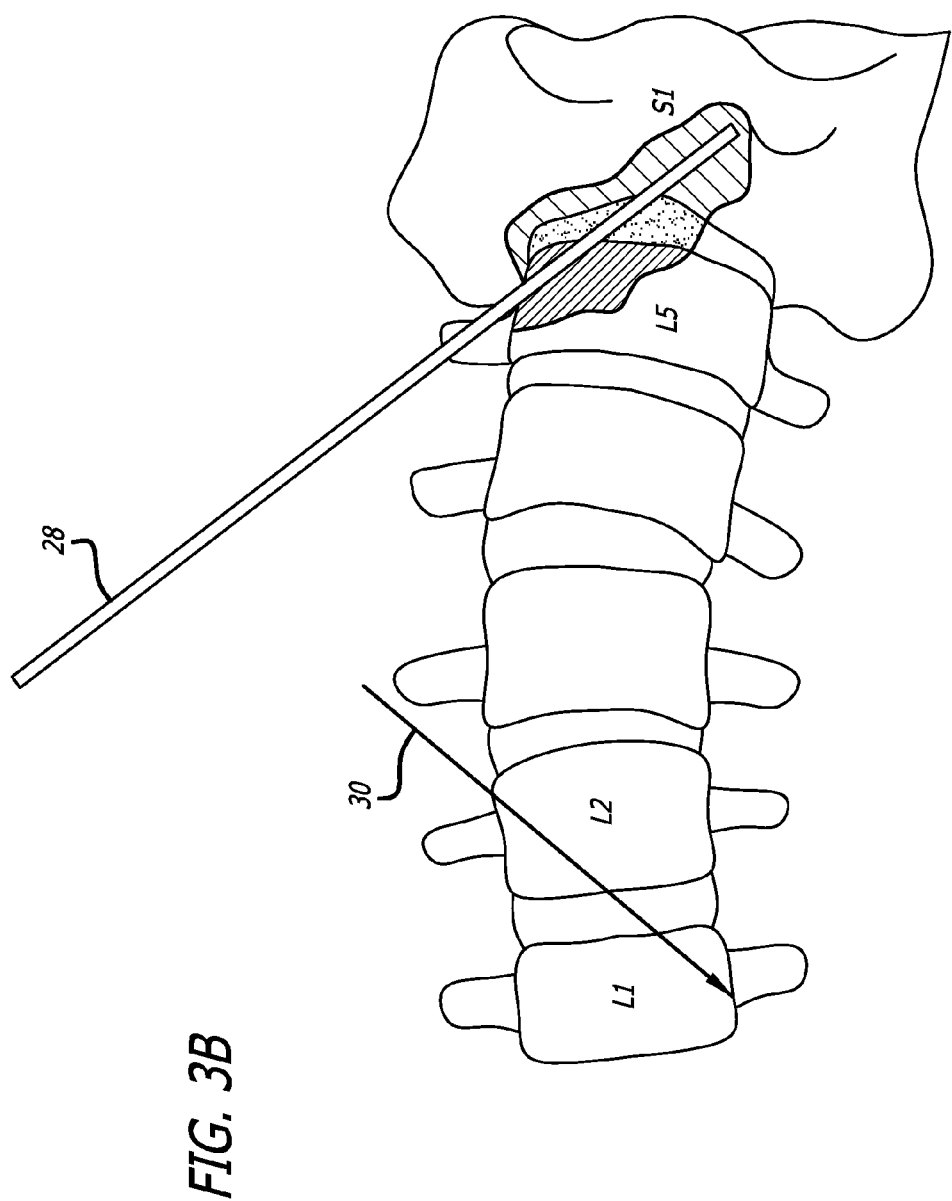
Figure 3C:
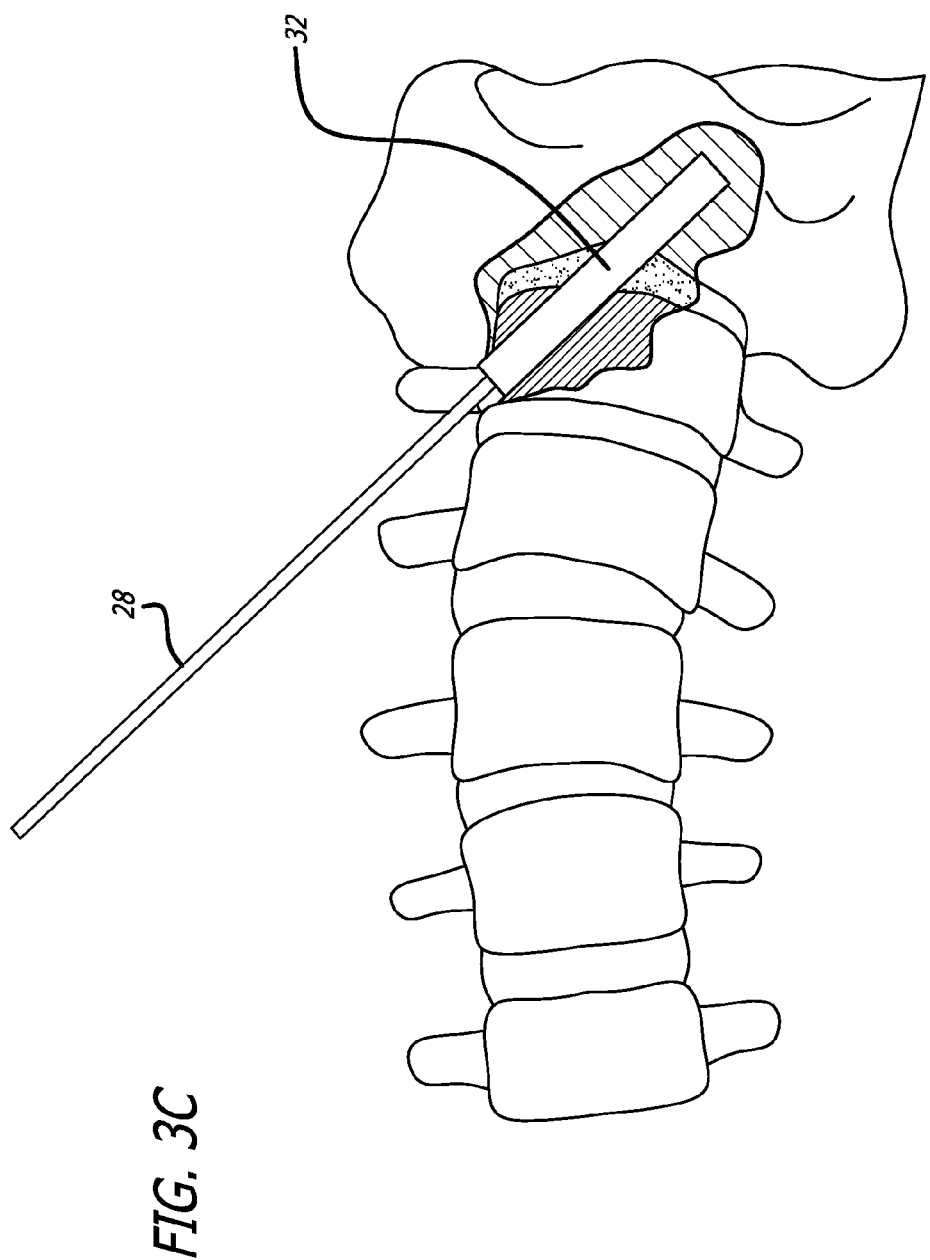
Figure 3D:
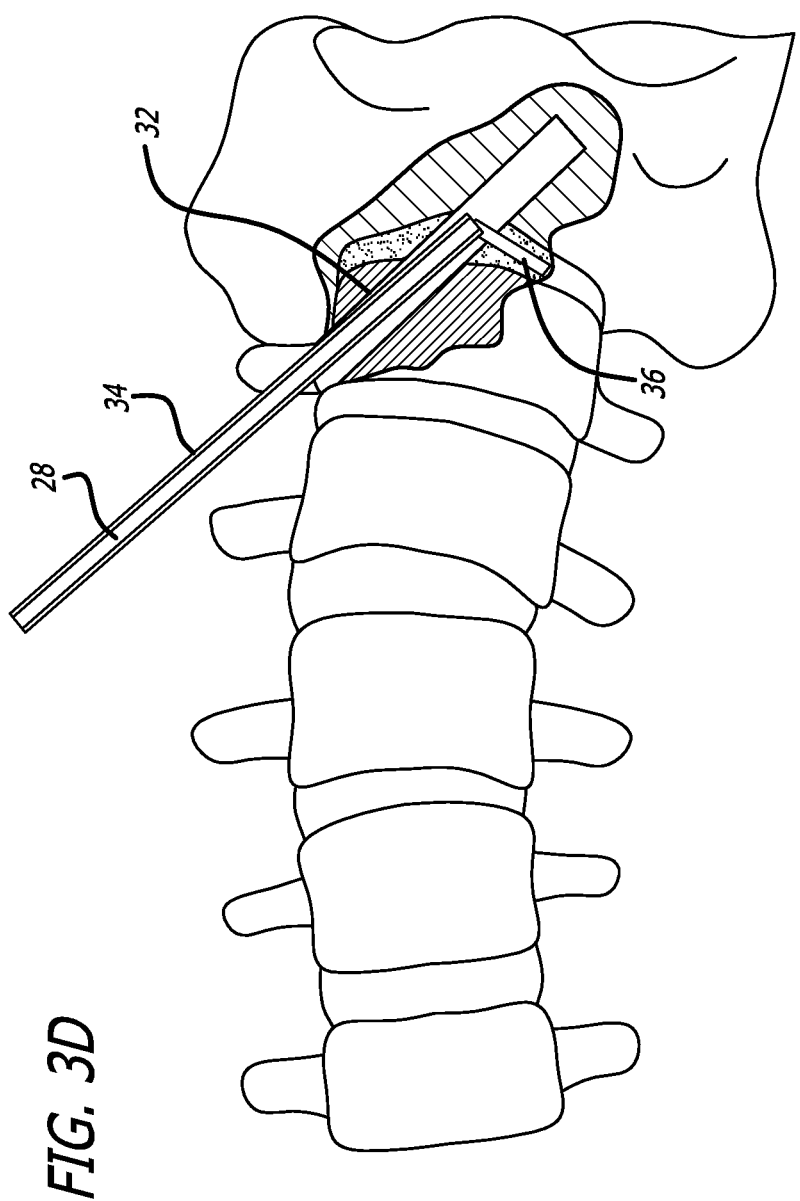
Figure 3E:
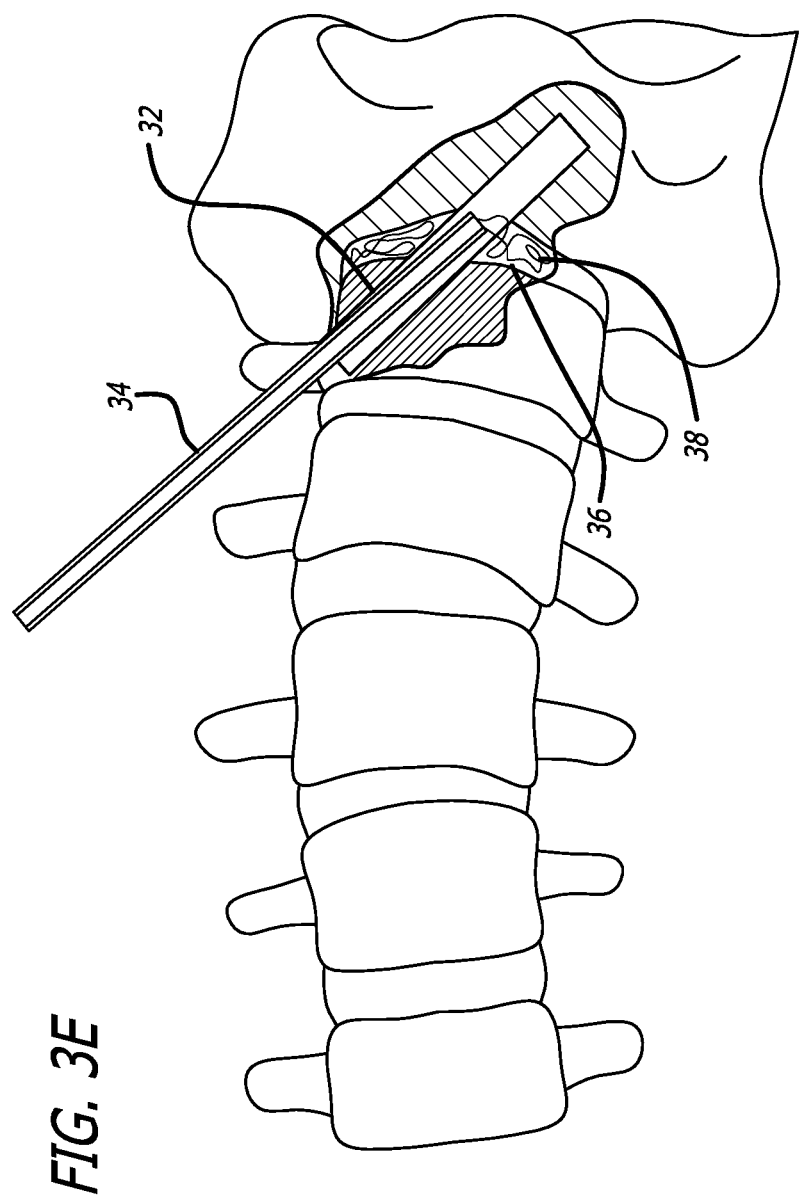

Although the above description provides an overview of embodiments of the lateral trans-psoas spinal fusion approach it should be understood that the insertion of the cage can include other additional supporting surgical steps (as shown in FIGS. 3a to 3e) including:

Dilation and then retraction of the muscle and flesh interposed between the surgical opening and the point at which the cage is first inserted into the superior vertebral body (e.g., in some embodiments the superior lateral edge of L-5) (note this step may or may not include using fluoroscopic retractor blades, as well as nerve monitoring to guide the lumbar plexus and neural monitoring to ensure safe passage by the exiting nerves) (FIG. 3a);

Passing a guidance wire (28) through the superior vertebral body then through the adjacent disc space and into the superior end of the inferior vertebral body (such a guide wire may be anchored in some embodiments 1 cm within the inferior vertebral body to ensure a secure anchor and guide point) (FIG. 3b) (Note, although this set of figures demonstrates the superior to inferior approach, as shown by the arrow (30) similar techniques may be used in an inferior to superior approach.);

Using the guide wire (28) and a series of drills (not shown) to drill and ream an opening (32) through the superior vertebral body via the lateral edge into the adjacent inferior disc space and then into the adjacent inferior vertebral body (during this process the interceding blood and marrow may be harvested via suction and stored, if desired, for later use) (FIG. 3c);

Preparing the disc space to expose the bony endplate of the inferior vertebral body (this can be done using any suitable curate, pituitary rongour and suction, and particularly an angled curate or rongour) (34), then an angled guide tube can be inserted into the prepared disc space (36) (FIG. 3d); and Inserting a cage (38) (preferably packed with previously harvested bone graft or other ortho-biological compounds) through the opening (32) thus created to anchor the cage into the disc space desired for fixation (36) (FIG. 3e).

Although the above discussion has focused on the fusion of L-5 and S-1, it will be understood that the technique of proceeding through a superior vertebral body into an inferior vertebral body can also be performed from an inferior vertebral body into a superior vertebral body, or across multiple vertebral bodies.

Turning to embodiments of the tools and system for performing a lateral trans-psoas spinal fusion, FIGS. 4 to 6 show various embodiments of distraction/retraction tools. In some embodiments, as shown in FIGS. 4a to 4g, there is a dilator (40) formed of a plurality of separate blades (42), each of which may be interconnected and joined into a whole defining an elongated conical cylinder (44). Although an embodiment showing four blades is shown in the figures, it should be understood that any number of blades more than two may be used in association with the dilator. To ensure the safe path of the blunt dilator through the nerve plexus, in some embodiments each of the blades is connected and monitored using a neuromonitoring system. Likewise, to ensure the dilators are secured at the correct docking position against the annulus of the disc fluoroscopic guidance may be incorporated into the dilator.

Regardless of the number of blades, it should be understood that the blades (42) are releasably interconnected through one or more suitable connectors, such as, latches, straps, pins, etc., such that when the dilator is in position, the blades may be separated into multiple independent segments or parts (FIGS. 4a and 4b) that may be moved radially away from one another to provide preliminary retraction of the soft tissue at the incision site. This ability to move radially outward in multiple directions provides better retraction and multiple directional neural monitoring. In addition, as shown in FIG. 4b, portions (46) of the blades (42) may be deformable (for example by segmentation of the blade) to expand the opening, prevent the distracted tissue from creeping over the blades, and to ensure that the blades do not restrict access to the surgical site. The blades (42) may also be formed with wire pins (48) to allow stable insertion into the underlying disc space. These wire pins may be integrated into or provided additional structures to on the blades, such as grooves, tabs, slots, etc., to secure the wire to the blade.

To further improve the positioning of the dilator, a guide wire may be inserted into or integrated with the dilator. It should be understood that any suitable guide wire design may be used such that the guide wire is sufficiently strong and has sufficient length to allow the guide wire to pass through the superior vertebral body and the adjacent disc space and anchor into the body of the inferior vertebral body, thereby creating a guiding path for the drills/reamers and cage. To accomplish the anchoring, the distal end of the guide wire may include any suitable form of terminating anchor tip capable of anchoring the distal end of the guide wire into the inferior vertebral body, including a spear, hook, threading, etc. The guide wire may also include neuromonitoring or fluoroscopic imaging to improve the accuracy of the guide wire positioning through the vertebral bodies and disc space.

Figure 4C:
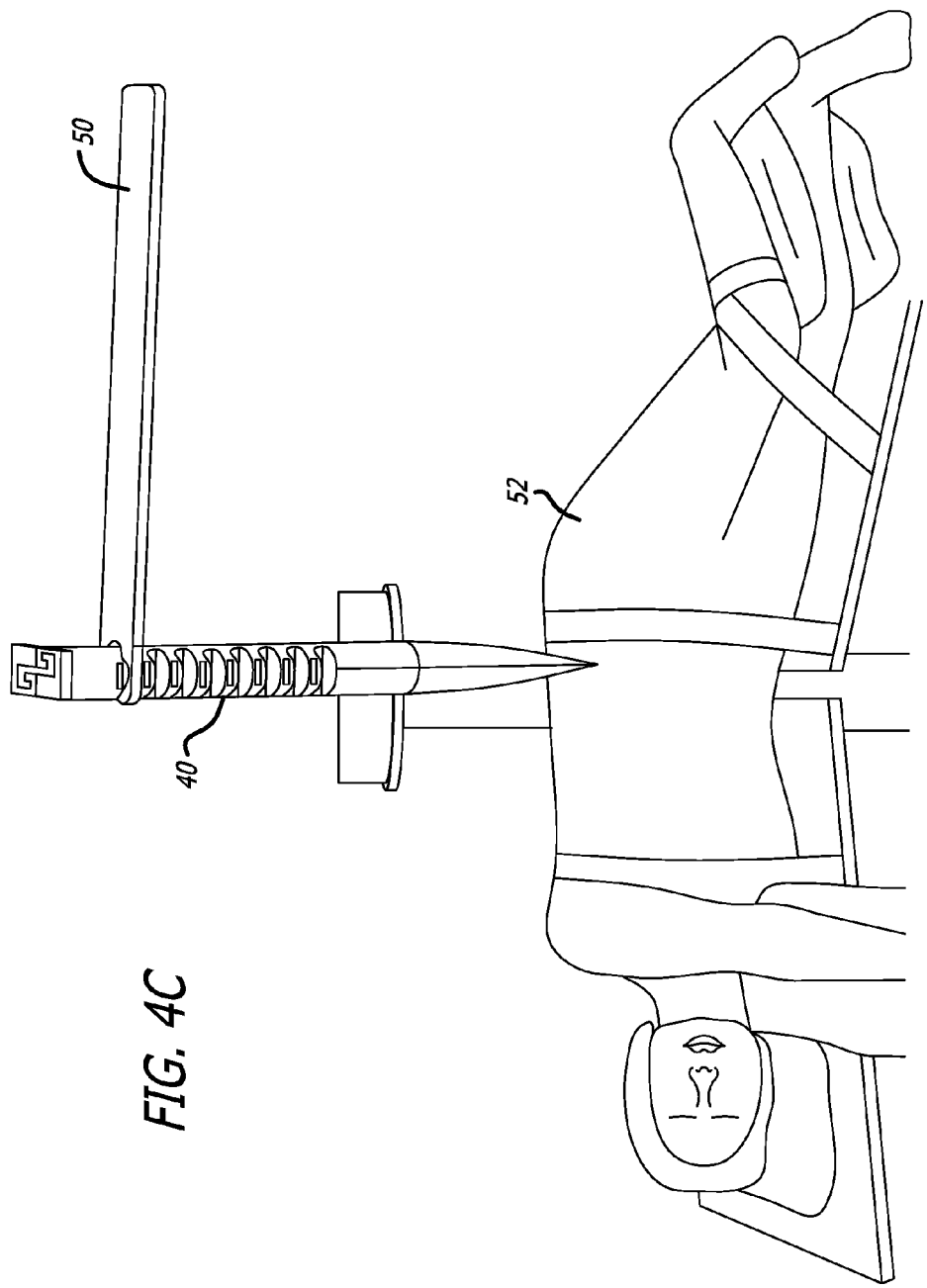
FIG. 4c provides a schematic view of a retractor tool in position for retraction in accordance with embodiments of the invention.

Operation of the dilator (40) requires positioning of the device above the surgical site. As shown in FIG. 4c, this may include the use of a dilator holder (50), such as a pitchfork, to keep the dilator in a stable and secure position in association with the patient's body (52). In this example, two separate and separable dilator/retractors are used, a two-bladed primary dilator and a two-bladed secondary dilator, however, it should be understood that these primary and secondary dilator functions could be combined in a single four or more bladed separable retractor.

Figure 4D:
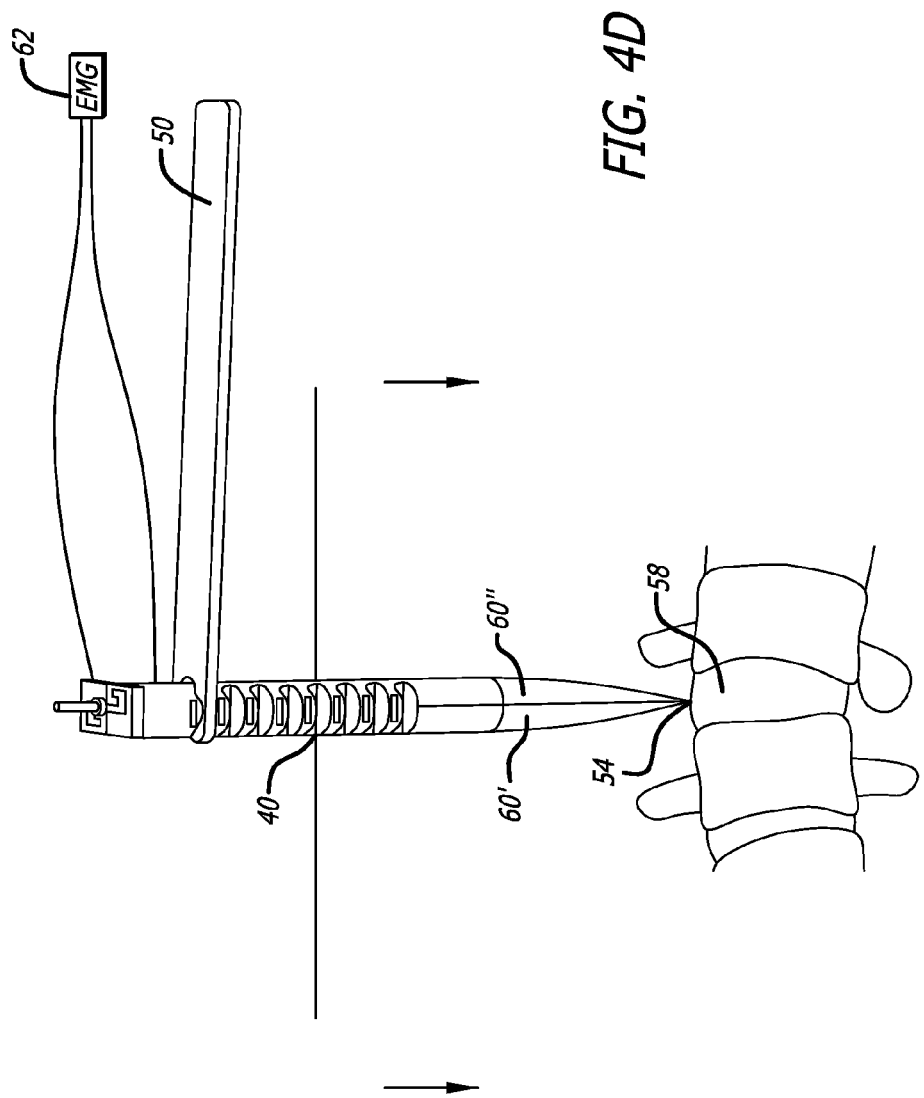
FIG. 4d provides a detailed schematic view of a retractor tool in position for retraction in accordance with embodiments of the invention.

As shown in FIG. 4d, in this embodiment, first the primary dilator (40) is inserted through the plexus and the nose of the dilator (54) is positioned at a retraction position at the disc space (58) to be distracted. To ensure proper positioning, each blade (60' and 60") can be separately connected to EMG monitoring (62).

Figure 4E:
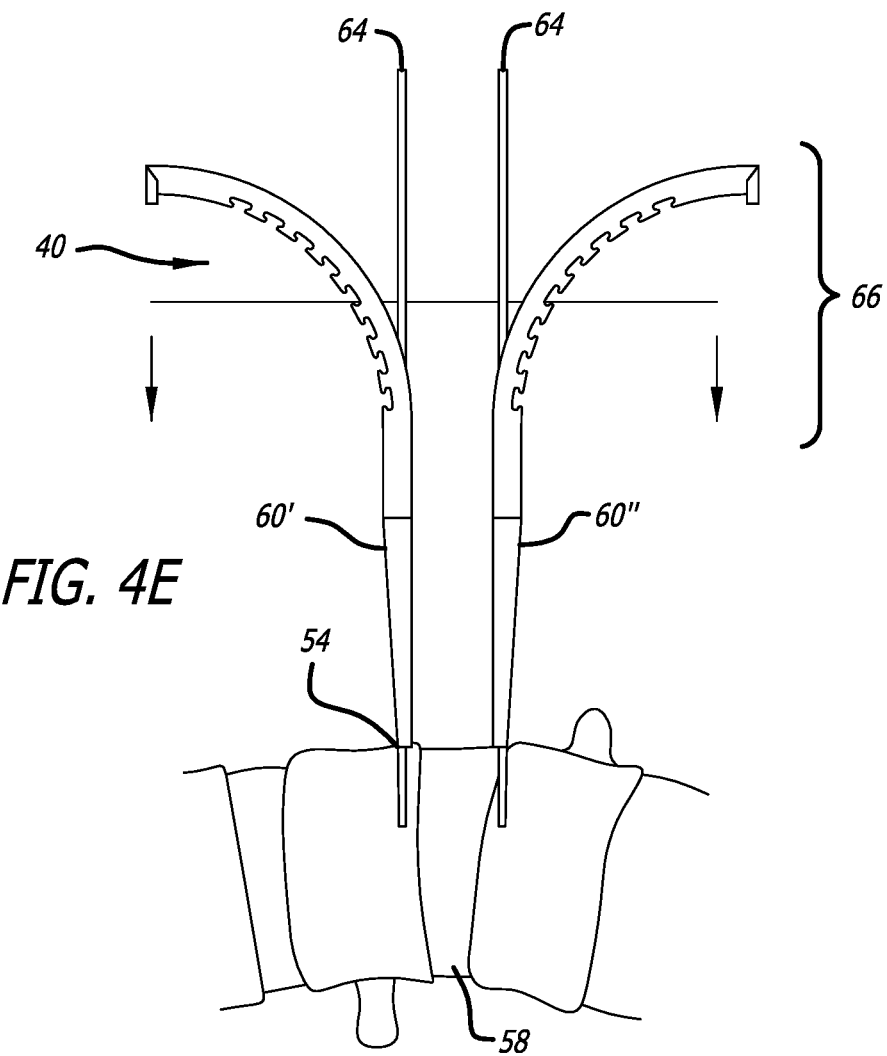
FIG. 4e provides a side view of a retractor tool in a retracted state in accordance with embodiments of the invention.
Figure 4E:
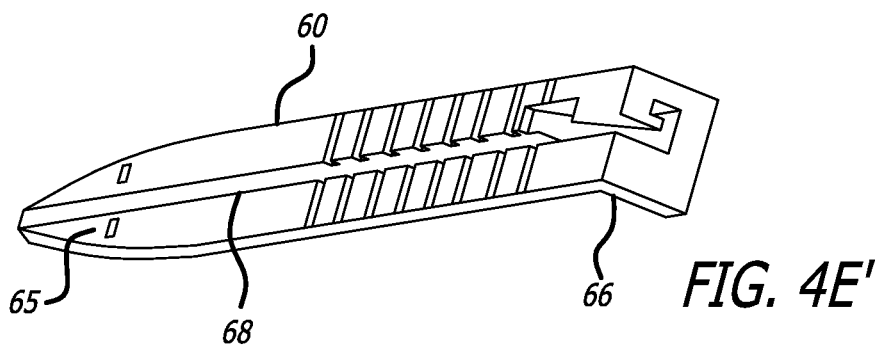

As shown in FIG. 4e, once the primary dilator is in position, the soft tissue is preliminarily retracted by moving the separable blades (60' and 60") of the dilator radially outward. To accomplish this, the retractor blades are deployed underneath the muscle to expose the annulus or bony surface. Once preliminary retraction is accomplished, wire pins (64) are inserted in conjunction with the retractor blades (60' and 60") and into the bone to anchor them in place. As shown in FIG. 4e', in some embodiments the retractor blades (60) comprise an elongated body having a proximal end (65) positioned at the disc space, and a distal (66) end that extends outside the body. As discussed previously, the distal portion (66) of the arms (60' and 60") may be made deformable so that they may be deformed (bent back) radially to contain the soft tissue and decrease the risk of soft tissue creeping underneath the retractor (40). The retractor blades may also be radiolucent to improve imaging and placement accuracy.

In many embodiments, the blades may also include a groove (68) into which the attachment wires (64) may be positioned such that the wires can be secured within the blades, and the blades can thus be secured to the underlying bone using the wires. In such embodiments, the terminal end of the attachment wires may include an anchor such as, for example, a point, hook or threading to anchor the wire securely into the bone. Preferably, the terminal end includes a stop (in preferred cases about 4 mm long) to prevent injury to the soft tissue under the bone. Although a groove is shown in the embodiments pictured, it will be understood that other configurations for holding the wire pin in place in relation to the blade may be used including slots, tabs, holes, etc.

Figure 4F:
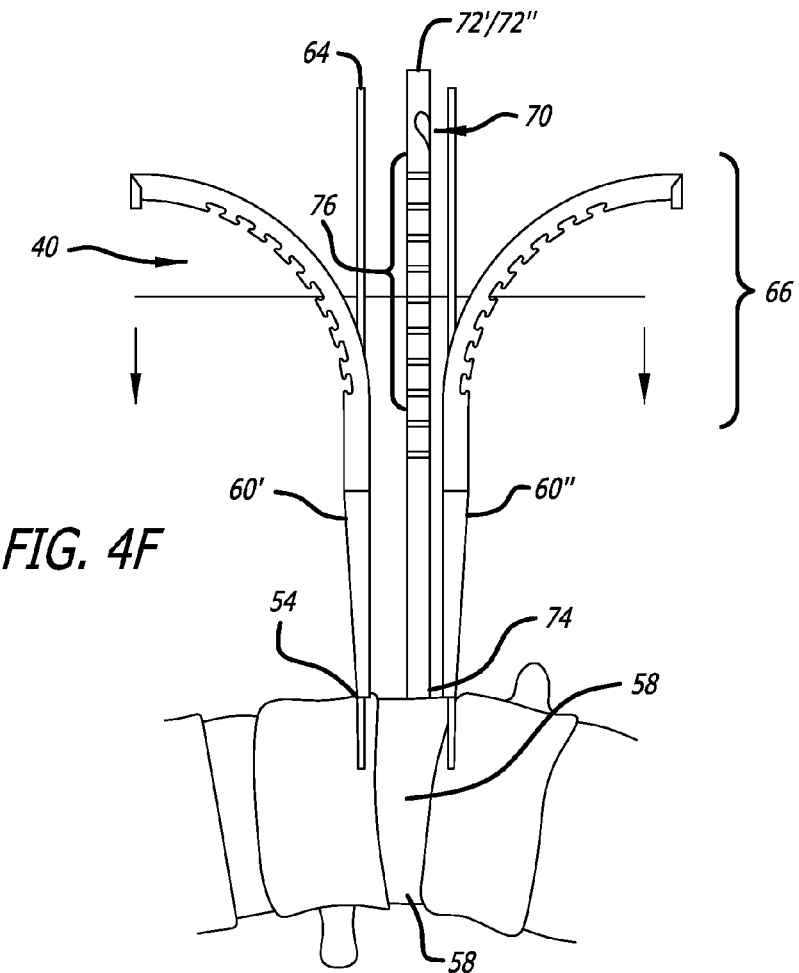
FIG. 4f provides a side view of a secondary retractor tool in accordance with embodiments of the invention.
Figure 4F:
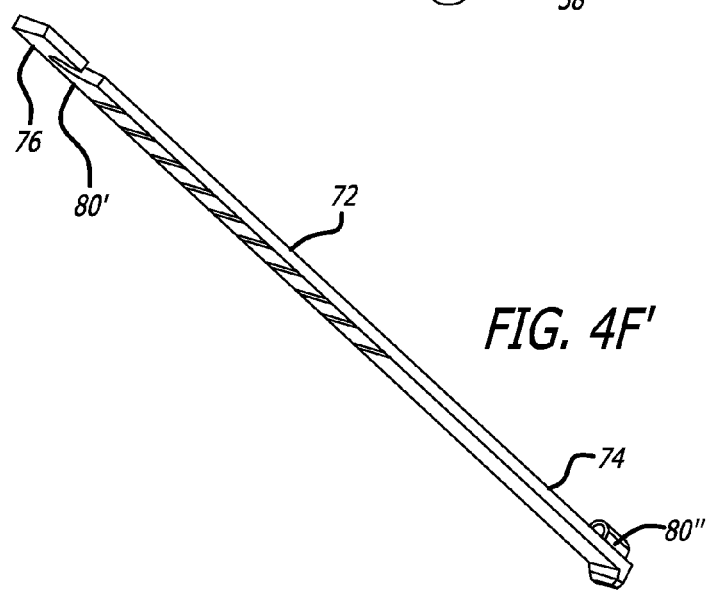

As previously discussed, in many embodiments the dilator includes a separate secondary retractor. As shown in FIG. 4f, in such embodiments once the primary retraction has been completed a separate secondary retractor (70) is positioned at the surgical site. In some embodiments this secondary retractor is arranged such that it retracts radially in a direction off-angle, or possible orthogonal, to the direction of the primary retraction. Although this secondary retractor may be formed of blades identical to those of the primary retractor, in some embodiments the secondary retractor is formed of blades (72' and 72") dimensioned and configured to be more compact than the primary retractor blades, and thus more easily used in conjunction with said primary retractor blades. Regardless of their dimensions, in many embodiments, the retractor blades (72' and 72") of the secondary retractor (70) are also formed of elongated bodies having a proximal end (74) designed to be positioned adjacent the disc space (58), and a distal end (76) designed to extend out of the body (see, FIG. 4f'). As with the primary retractor, the distal portions (76) of the secondary retractor may be deformable (such as by forming deformable portions along the length of the distal end) such that they may be radially deformed (bent back) to contain the soft tissue and decrease the risk of soft tissue creeping underneath the retractor. These secondary retractor blades may also be radiolucent to improve imaging and placement accuracy.

Once the retractor blades (72' and 72") are retracted as desired, wire pins (78 in FIG. 4g) may then be inserted in conjunction with the retractor blades and into the bone to anchor them in place. In many such embodiments, the blades may include a groove or other securing mechanism (as discussed above with respect to FIGS. 4e and 4e') into which the attachment wire pins may be positioned such that the wires can be secured within the blades. In the embodiment shown in FIGS. 4f and 4f' the securing mechanism includes independent slots (80' and 80") disposed at the proximal and distal ends of the blades into which the pins may be inserted and then secured to the underlying bone. As discussed before, in such embodiments, the terminal end of the attachment wires may include an anchor such as, for example, a point, hook or threading to anchor the wire securely into the bone. Preferably, the terminal end includes a stop (in preferred cases about 4 mm long) to prevent injury to the soft tissue under the bone.

Figure 4G:
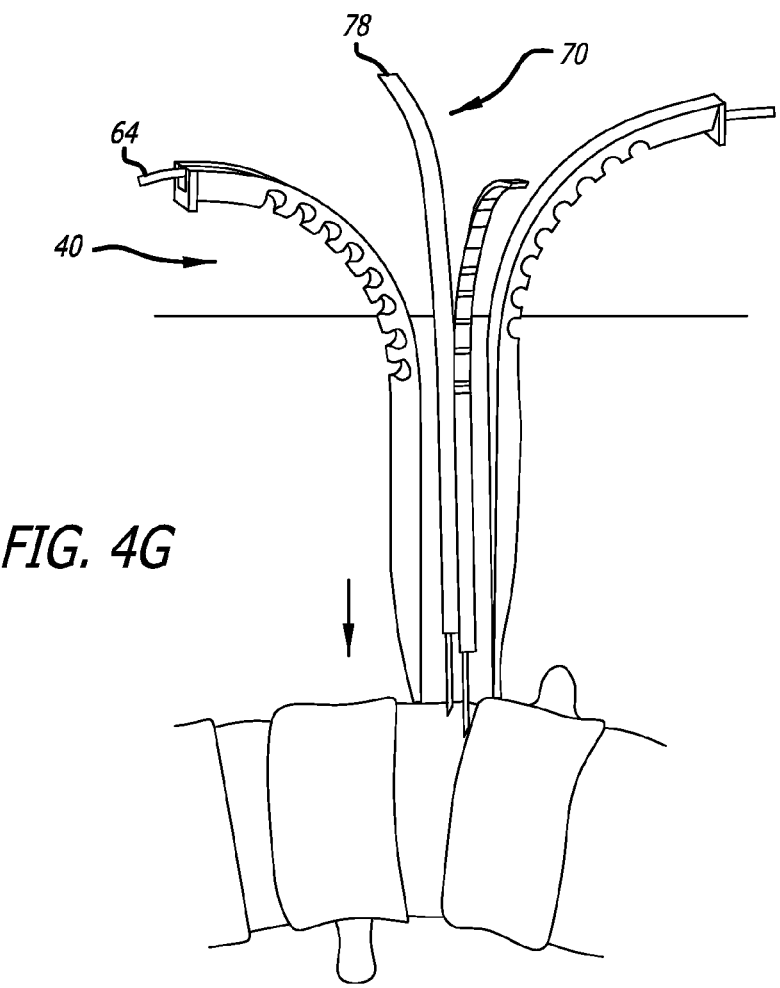
FIG. 4g provides a side view of primary and secondary retractor tool in retracted states in accordance with embodiments of the invention.
Figure 4G:
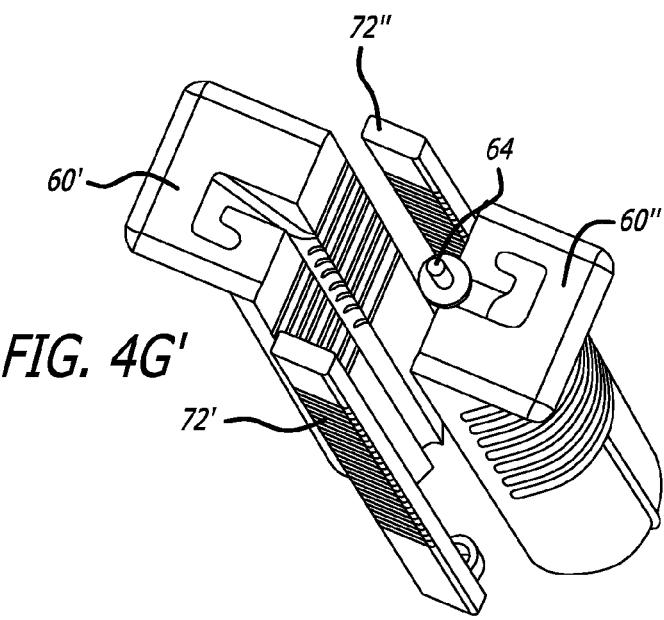

As shown in FIGS. 4g and 4g', once the retractors (40) and (70) are in position, the distal ends of the wire pins (64) and (78) are bent back to secure the retractor blades in position. It should be understood that although embodiments using multiple, separable two-bladed retractors are described above, a single four-bladed retractor may be used or even retractors with higher numbers of blades of similar radially separable blade designs.

Regardless of the design, the dilator and retractor may be used in association with conventional drills, reams, curates, rongours, suction devices, etc. to form a borehole through the vertebral bodies and to prepare the disc space between said bodies. It should be understood that this list is not meant to be exclusive, and other tools or supporting devices may be used in conjunction with the described dilator/retractor as necessary to support the surgery.

Figure 5A:
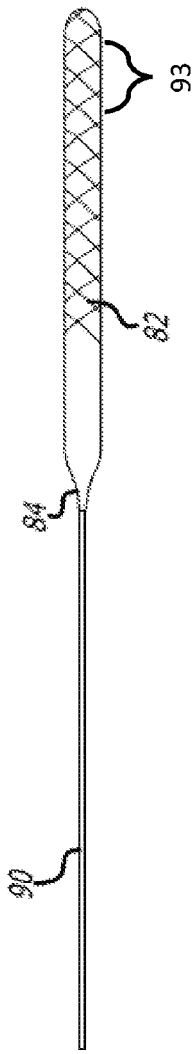
FIG. 5a provides a side view of an unexpanded interbody cage in accordance with embodiments of the invention.
Figure 5B:
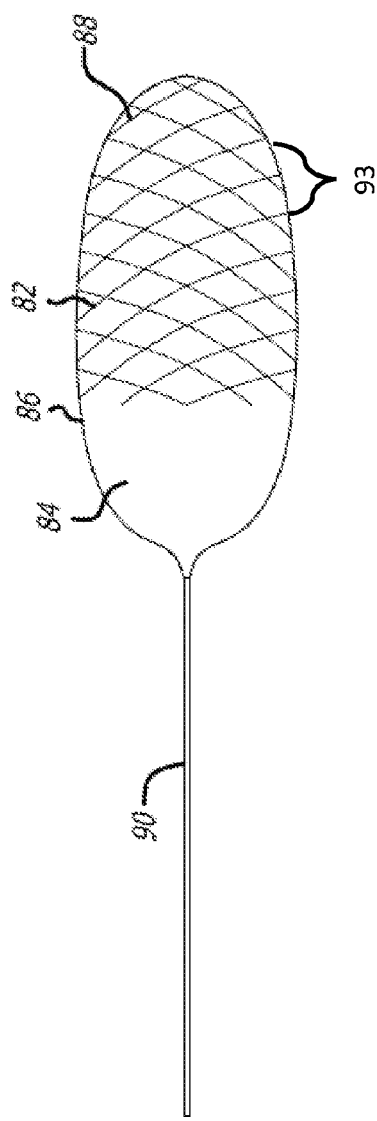
FIG. 5b provides a side view of an expanded interbody cage with a fully inflated expansion element inserted therein in accordance with embodiments of the invention.
Figure 5C:
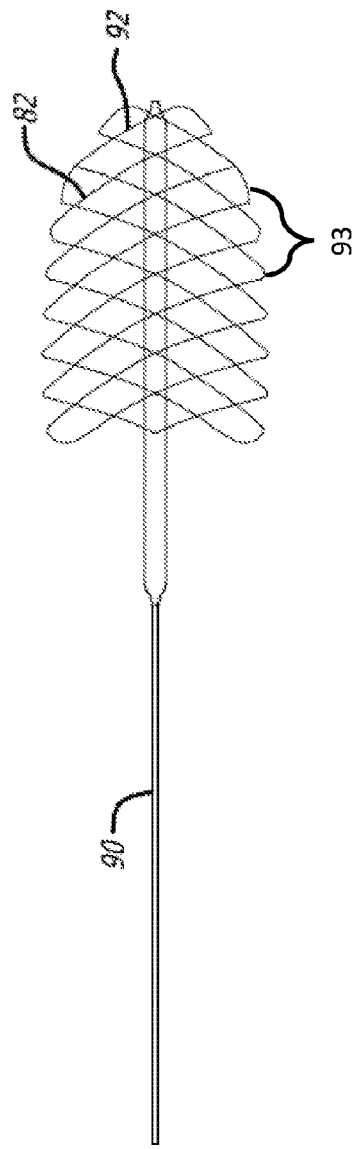
FIG. 5c provides a side view of an expanded interbody cage with a deflated expansion element in accordance with embodiments of the invention.

An expandable vertebral body cage system may also be used in association with the trans-psoas approach. Embodiments of the expandable cage system are shown in FIGS. 5a to 5c. This cage system may be used in association with any disc space or minimally invasive approach as it allows for the collapsed cage to assume a minimal cross-section during insertion and prior to expansion.

FIG. 5a shows a side view of a collapsed interbody cage (82) having disposed within an expandable element (84) in accordance with embodiments. Although the cage may have features in common with the balloon-expandable stents commonly found in the vascular field, it will be understood that since the cage is required to maintain the disc space between the adjacent vertebral bodies it must be composed of a material having far greater strength. As shown in FIGS. 5a to 5c, in some embodiments the cage takes the form of a cylindrical body formed of an interwoven mesh of elements that can be collapsed and then expanded by exposure to an outward radial force. Because the interwoven elements can be highly compressed it is possible to advance the cage to the delivery site within the context of a minimally invasive approach through, for example, a bent entry tube. Although one mesh design is shown in FIGS. 5a to 5c, it will be understood that numerous designs are possible that would allow expansion of such a cage.

Although the cage (82) shown in FIG. 5a includes a substantially cylindrical body, it should be understood that the cage may take any cross-section (either symmetric or non-symmetric) and may incorporate changes in cross-section from its proximal end (86) to the distal terminating end (88), such as tapering, undulations, threading, etc. The cylindrical body is at least partially hollow allowing for the insertion of the expandable element (84) within the body. In addition, the hollow body may be formed to allow for the incorporation of bone graft materials, such as bone morphogenic protein and derivatives, inside of the cage, thereby allowing the cage to be fused and incorporated into the bony structure of the adjacent vertebrae once the cage is inserted and expanded. The cages can likewise incorporate a removable thin sleeve that prohibits or minimizes side leakage through the cage prior to expansion.

Threading and cutting elements (93) may also be disposed along the outer surface of the cage. The threading and cutting flutes, where provided, should be long enough to allow the cage to be screwed through the borehole formed in the vertebral bodies and disc space with a tool such as a ratchet, driver, insertion rod, etc. Likewise, any cutting flutes should be long enough to broach through the cartilage of the vertebral endplates and into the bony tissue, thereby making the cage "self-broaching", that is able to broach through the cartilaginous endplates of a vertebra on its own, exposing subchondral bone.

FIG. 5b shows the cage (82) of FIG. 5a after expansion of the internal expandable element (84). Any suitable expandable element may be used with the cage. In some embodiments, the expandable element (84) is a balloon or other inflatable member that is interconnected through a lumen (90) to a source of pressurization. In such an embodiment, once the disc is in place the expandable element would be pressurized, which would in turn exert a radial force on the collapsed cage. Although a single monolithic expandable balloon element is shown in FIG. 5b, it will be understood that the expandable element may include multiple balloons that may be inflated simultaneously or separately through a single or multiple lumens. Moreover, although pressurized balloons are described above, it will be understood that other possibilities for expandable elements include resilient, mechanical and electromechanical elements.

Finally, FIG. 5c shows the cage (82) of FIGS. 5a and 5b after deflation of the internal expandable element (84). Once deflated the expandable element may be removed while the cage remains secured within the desired disc space. Although the interior cavity of the cage (82) in this embodiment is shown as completely open, it should be understood that the cage may be provided with any number and arrangement of rigid internal members or ribs to stabilize and increase the center strength of the generally hollow cage.

As shown in the side view of FIGS. 5b and 5c, the cage (82) has fenestrations (92), or openings, along its sides. These fenestrations allow bone graft within the main body of the cage to exit and fuse with adjacent vertebrae outside of the cage. Although these fenestrations are disposed as a mesh all about the perimeter of the cage in the embodiment shown in FIGS. 5a to 5c, it should be understood that they may take any conformation along the cage. It should also be understood that these fenestrations may be positioned anywhere along the cage body provided at least one fenestration is disposed such that when the cage is in position the fenestration opens into the disc space to be fused, thereby allowing the orthotic material to enter into the disc space and fuse the adjacent vertebral bodies.

Figure 6A:
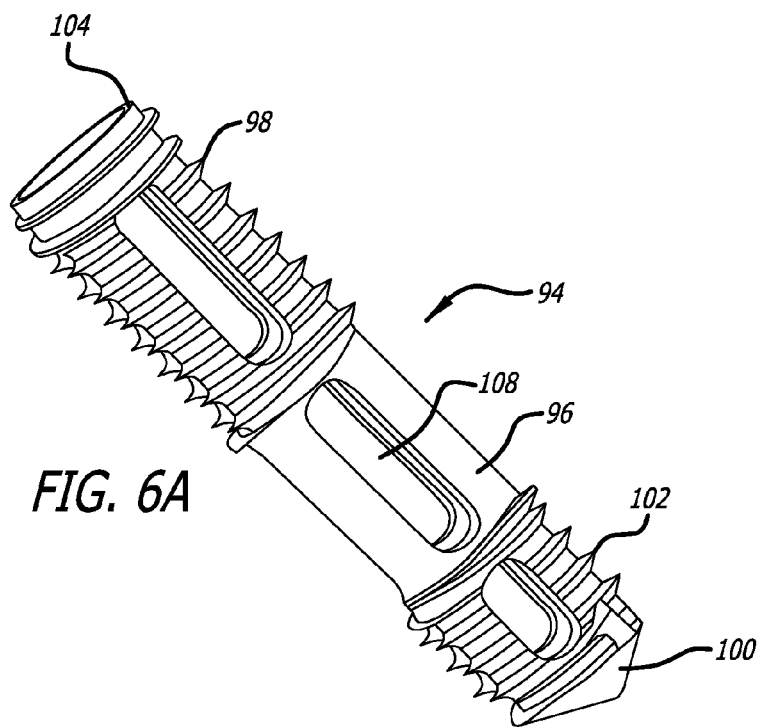
FIGS. 6a and 6b provide side views of fusion cage screws in accordance with embodiments of the invention.
Figure 6B:
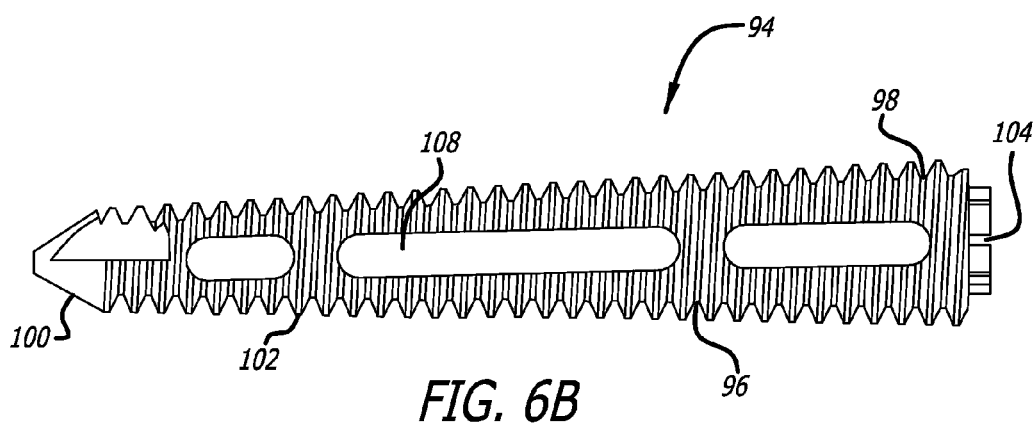
Figure 6C:
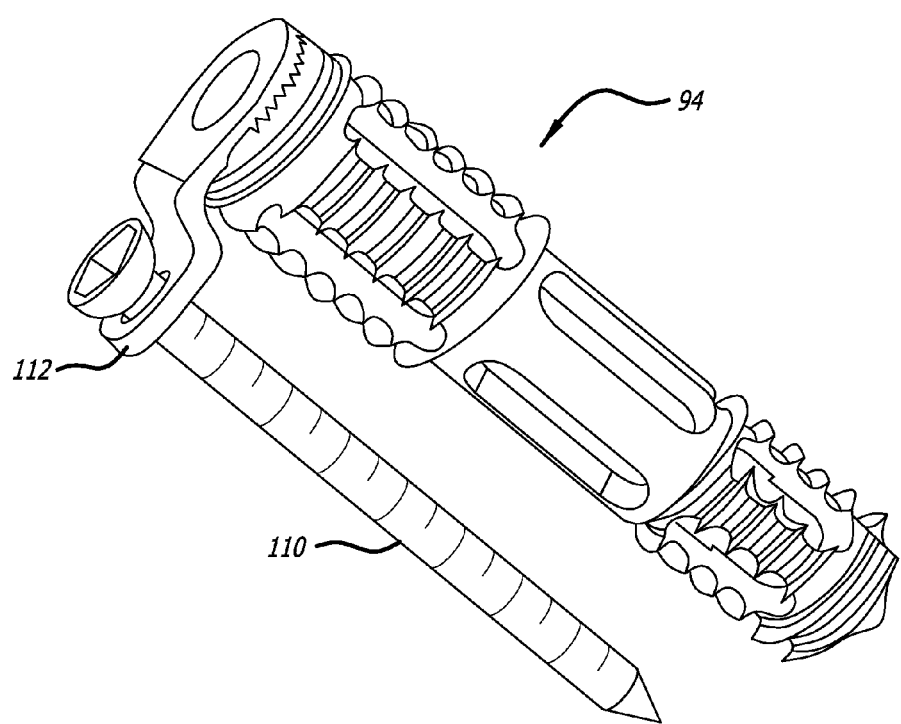
FIG. 6c provides a side view of a fusion cage screw with de-rotation screw in accordance with embodiments of the invention.

In addition to the interbody cages, a separate threaded cage-screw may be used to stabilize the access hole drilled through the vertebral bodies and the intervening disc space. FIGS. 6a to 6c show a number of embodiments of such stabilizing screw cages. FIG. 6a shows a side view of an exemplary threaded interbody cage screw (94) in accordance with embodiments. The cage screw (94) includes a substantially cylindrical body (96) that may be configured to taper from the proximal end (98) to the distal terminating end (100), as shown in FIG. 5b. The cylindrical body is at least partially hollow allowing for bone graft with biological materials, such as morphogenic protein and derivatives, to be placed inside of the cage, thereby allowing the cage to be fused and incorporated into the bony structure of the adjacent vertebrae once the cage is inserted.

Regardless of the overall shape of the threaded stabilizing cage screw, a threading (102) runs along the outer surface of the cage (94) from proximal to distal ends. This threading allows the cage to be screwed through the borehole formed in the vertebral bodies and disc space. The proximal end of end of the cage may be provided with an engagement point (104) to allow a tool such as a ratchet, driver, insertion rod, etc. to engage the cage and rotatively drive the cage into the borehole using the threading. Although not shown, cutting element may also be disposed along the outer surface of the cage. The cutting flutes, where provided, should be long enough to broach through the cartilage of the vertebral endplates and into the bony tissue, thereby making the cage "self-broaching", that is able to broach through the cartilaginous endplates of a vertebra on its own, exposing subchondral bone. The interior cavity of the cage, although not shown, may be provided with any number and arrangement of rigid to stabilize and increase the center strength of the generally hollow cage.

As shown in the side views of FIGS. 5a and 5b, the cage (94) may have fenestrations (108), or openings, along its sides. These fenestrations allow bone graft within the main body of the cage to exit and fuse with adjacent vertebrae outside of the cage. Although in the pictured embodiment these fenestrations are disposed about mid-point along the cage, it should be understood that these fenestrations may be positioned anywhere along the cage body provided at least one fenestration is disposed such that when the cage is in position the fenestration opens into the disc space to be fused, thereby allowing the orthotic material to enter into the disc space and fuse the adjacent vertebral bodies.

In some embodiments, as shown in FIG. 5c, the cage is provided with an additional anchoring screw (110), which is attached via an armature (112) to at least the proximal end of the cage (94). During use, the cage would be threaded into the borehole (as described above) and then once in final position the additional anchoring screw (110) would be inserted into the armature and the anchored into the superior vertebral body. The insertion of this additional anchoring screw would then prevent any further rotation or back-out of the cage from the vertebral bodies once the cage is in its final fusion position.

Figure 7A:
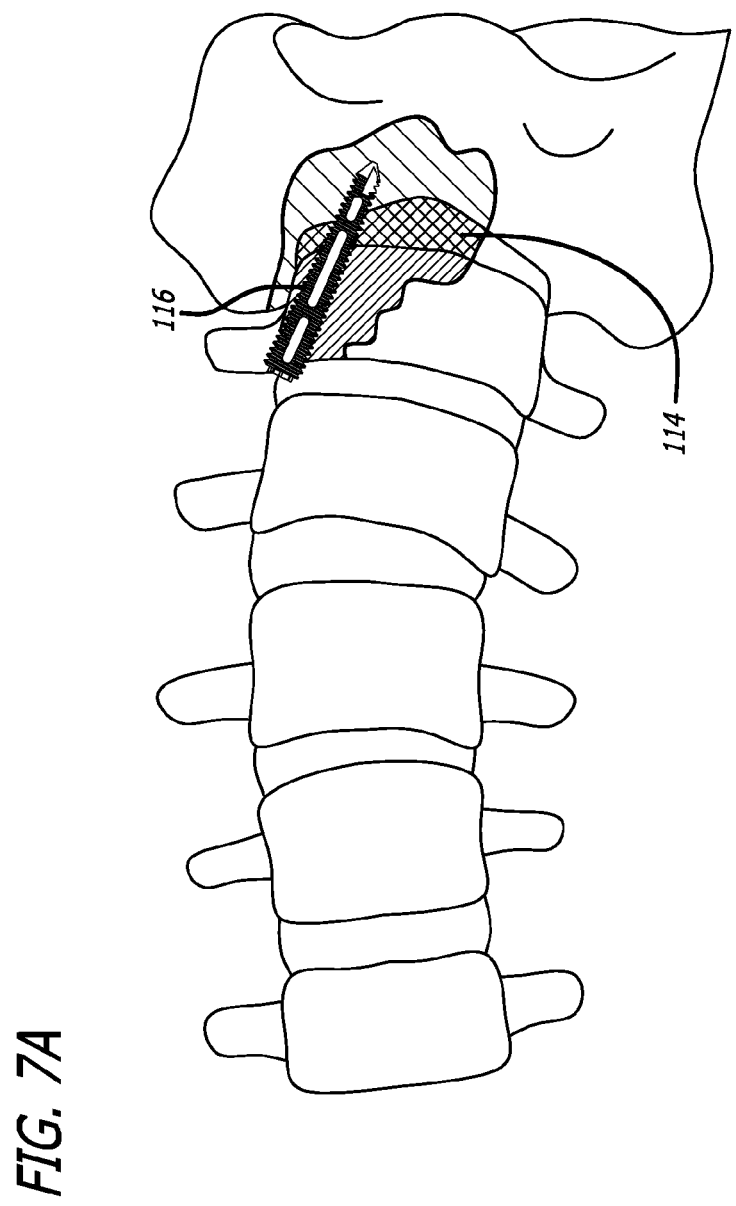
FIGS. 7a and 7b provide schematic views of the use of the interbody and fusion cages in a minimally invasive surgical technique in accordance with embodiments of the invention.
Figure 7B:
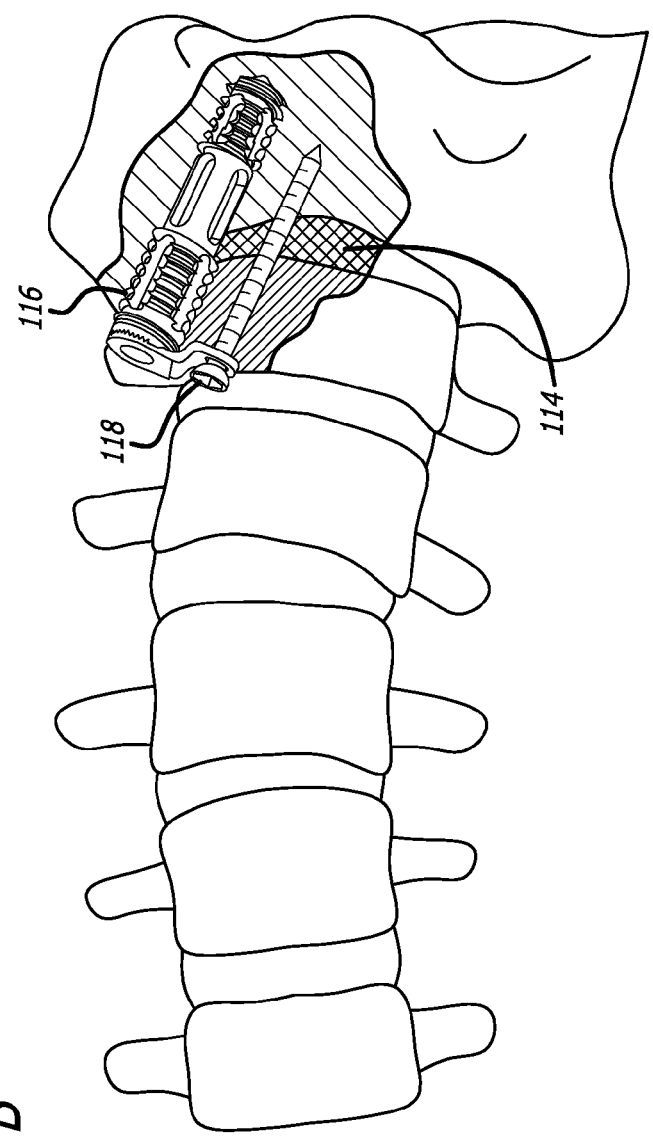

Although the above discussion has focused on particular tools for use in association with a trans-psoas approach, it will be understood that the invention is also directed to methods of spinal fusion using such tools. In some embodiments, the spinal fusion method includes the insertion of an interbody cage (114) via a minimally invasive approach. In such embodiments, the collapsed vertebral body cage (114), as shown in FIG. 6a is inserted and inflated into a prepared disc space. As discussed above, within this cage may be incorporated bone or ortho-biological compounds such that bridging bone may grow within the cage to achieve arthrodesis between the adjacent vertebrae. Once the cage is expanded, the expandable element is deflated, as shown in FIG. 5c, and removed from within the cage. Once the interbody cage is inserted the access hole drilled through the vertebral bodies and disc space may be stabilized using a threaded stabilizing cage screw (116) (which may or may not include and additional stabilizing screw (118)), as shown in FIGS. 7a and 7b. Although the cages may be used in other approaches, they may particularly be used in association with a lateral trans-psoas surgical fusion method to fuse the space between the L-5 and S-1 vertebral bodies.

Although the above description provides an overview of a suitable minimally invasive spinal fusion approach it should be understood that the insertion of the cage may include many additional supporting surgical steps including:

Dilation and then retraction of the muscle and flesh interposed between the surgical opening (note this step may or may not include using fluoroscopic retractor blades, as well as nerve monitoring to guide the lumbar plexus and neural monitoring to ensure safe passage by the exiting nerves)(as discussed above in association with FIGS. 3a and 4a to 4f);

Passing a guidance wire adjacent to the desired disc space (such a guide wire may be anchored to ensure a secure anchor and guide point) (FIG. 3b), and using the guide wire and a series of drills to drill and ream an opening) to gain access to the target disc space (during this process the interceding blood and marrow may be harvested via suction and stored, if desired, for later use) (FIG. 3c);

Exposing the adjacent disc space and the preparing the disc space by performing a diskectomy (this can be done using any suitable angled curate, pituitary rongour and suction) (FIG. 3d); and Inserting the expandable interbody cage, and additionally a stabilizing cage screw (preferably packed with previously harvested bone graft or other ortho-biological compounds) through the openings thus created to anchor the cages into place in the disc space and drilled passage, and securing the cages in place (FIG. 3e).

Although the above discussion provides schematics relevant to the fusion of L-5 and S-1, it will be understood that the technique may be used in any minimally invasive approach where a disc replacement is desired on either single or multiple levels.

In each of the embodiments discussed above, the tools and implants preferably would be formed of a suitable biologically inactive material, such as, titanium, stainless steel, alloys or carbon fiber. Alloys such as porous titanium-nickel alloy have been shown to promote rapid tissue ingrowth and can be used herewith. Likewise, the fenestrated walls and threadings of the cage can be cut or stamped out from metal or absorbable biological material mesh prior to cage formation.

Although specific embodiments are disclosed herein, it is expected that persons skilled in the art can and will design alternate embodiments and methods that are within the scope of the following claims either literally or under the doctrine of equivalents.

What is claimed is:

1. A method for performing a lateral trans-psoas spinal fusion procedure comprising:
    forming a surgical opening at a fusion site;
    inserting a plurality of releasably interconnected retractor blades into the surgical opening and moving them radially outward in a plurality of directions such that the retractor blades dilate and retract muscle and flesh within the surgical opening to form a passageway through a lumbar plexus at the fusion site to expose a lateral edge of a primary vertebral body;
    associating a wire pin with each of the retractor blades and inserting each of the wire pins into the lateral edge of the primary vertebral body to anchor each of the retractor blades into their retracted positions thereby stabilizing the passageway;
    forming an access opening in the lateral edge of and through the primary vertebral body to allow access to the disc space between the primary vertebral body and an adjacent vertebral body;
    preparing and distracting the disc space between the primary and adjacent vertebral bodies to expose a bony endplate of the adjacent vertebral body;
    inserting an interbody cage having external cutting elements, a plurality of fenestrations formed in an outer surface thereof, and an internal cavity into which is disposed a graft material and a removable expandable element through the primary vertebral body and into the disc space, and anchoring the cutting elements of the interbody cage in at least the bony endplates of the primary and adjacent vertebral bodies;
    expanding the expandable element to expand the interbody cage within the disc space;
    deflating the expandable element and removing the expandable element from the surgical opening by passing it through the access opening in the primary vertebral body; and
    threading a cylindrical cage, having a threading disposed about its outer circumference and a fenestrated internal cavity having disposed within a graft material, through the access opening in the primary vertebral body and into the adjacent vertebral body such that it passes through the disc space to stabilize the access opening in the primary vertebral body.

2. The method of claim 1, wherein the primary vertebral body is superior to the adjacent vertebral body, and wherein the access opening is formed in the lateral edge of the superior vertebral body and the cylindrical cage anchored in at least the bony endplate of the adjacent vertebral body.

3. The method of claim 1, wherein the graft material incorporates bone or ortho-biological compounds.

4. The method of claim 1, wherein the superior vertebral body is L-5 and the inferior vertebral body is S-1.

5. The method of claim 1, further comprising radially deforming a portion of each of the retractor blades external to the surgical opening such that the deformed portion of the retractor blades contain the tissue around the surgical opening.

6. The method of claim 1, wherein the step of dilating and retracting tissue includes retracting a primary pair of retractor blades disposed opposite each other, followed by retracting a secondary pair of retractor blades disposed at an off-angle from the primary set of retractor blades.

7. The method of claim 1, wherein the step of dilating and retracting tissue includes the use of nerve monitoring.

8. The method of claim 1, wherein the step of dilating and retracting tissue includes the use of fluoroscopic retractor blades.

9. The method of claim 1, further comprising inserting a guidance wire through the primary vertebral body and the adjacent disc space and into the adjacent vertebral body.

10. The method of claim 1, wherein the step of forming the access opening in the lateral edge of the primary vertebral body comprises drilling and reaming.

11. The method of claim 10, wherein the drilling and reaming occurs along a guidance wire disposed through the primary vertebral body and the adjacent disc space and into the adjacent vertebral body.

12. The method of claim 10, wherein the drilling and reaming further comprises harvesting blood and marrow via suction.

13. The method of claim 1, wherein the primary vertebral body is inferior to the adjacent vertebral body, and wherein the access opening is formed in the lateral edge of the inferior vertebral body and the cylindrical cage anchored in at least the inferior bony endplate of the adjacent vertebral body.

14. The method of claim 1, wherein the fusion occurs across multiple vertebral bodies.

\* \* \* \* \*